（12）United States Patent
Marshall et al.

(10) Patent No.: US 8,206,308 B2
(45) Date of Patent: Jun. 26, 2012

(54) SHIELDING FOR INTRAVASCULAR ULTRASOUND IMAGING SYSTEMS AND METHODS OF MAKING AND USING

(75) Inventors: John D. Marshall, Los Gatos, CA (US); Donald Masters, Fremont, CA (US)

(73) Assignee: Boston Scientific SciMed, Inc., Maple Grove, MN (US)

( * ) Notice: Subject to any disclaimer, the term of this patent is extended or adjusted under 35 U.S.C. 154(b) by 517 days.

(21) Appl. No.: 12/435,258

(22) Filed: May 4, 2009

(65) Prior Publication Data

US 2009/0275838 A1    Nov. 5, 2009

Related U.S. Application Data

(60) Provisional application No. 61/050,616, filed on May 5, 2008.

(51) Int. Cl.
*A61B 8/14*    (2006.01)

(52) U.S. Cl. ........ 600/466; 600/407; 600/463; 600/467; 600/461

(58) Field of Classification Search .......... 600/407, 600/437, 463, 466, 439, 461, 467
See application file for complete search history.

(56) References Cited

U.S. PATENT DOCUMENTS

| | | | |
|---|---|---|---|
| 4,674,515 A | 6/1987 | Andou et al. | |
| 5,921,931 A | 7/1999 | O'Donnell et al. | |
| 5,924,993 A | 7/1999 | Hadjicostis et al. | |
| 6,099,471 A | 8/2000 | Torp et al. | |
| 6,251,078 B1 | 6/2001 | Moore et al. | |
| 6,945,938 B2 | 9/2005 | Grunwald | |
| 7,037,271 B2 * | 5/2006 | Crowley | 600/463 |
| 7,169,165 B2 | 1/2007 | Belef et al. | |
| 7,235,061 B2 | 6/2007 | Tsugita | |
| 7,306,561 B2 | 12/2007 | Sathyanarayana | |
| 2001/0016688 A1 | 8/2001 | Moore et al. | |
| 2001/0029337 A1 * | 10/2001 | Pantages et al. | 600/463 |
| 2005/0038342 A1 | 2/2005 | Mozayeni et al. | |
| 2006/0030777 A1 | 2/2006 | Liang et al. | |
| 2006/0100522 A1 | 5/2006 | Yuan et al. | |
| 2006/0173350 A1 | 8/2006 | Yuan et al. | |
| 2006/0253028 A1 | 11/2006 | Lam et al. | |

(Continued)

FOREIGN PATENT DOCUMENTS

EP    0 871 043 B1    6/2004

(Continued)

*Primary Examiner* — Brian Casler
*Assistant Examiner* — Joel Lamprecht
(74) *Attorney, Agent, or Firm* — Frommer Lawrence & Haug LLP; Bruce E. Black (57) ABSTRACT

A catheter assembly for an intravascular ultrasound system includes a catheter, an imaging core, and a shield-coupling capacitor. The catheter defines a lumen extending along a longitudinal length of the catheter. The imaging core is configured and arranged for inserting into the lumen. The imaging core includes a rotatable driveshaft, one or more transducers, one or more conductors, and a conductive shield. The one or more transducers are mounted to the rotatable driveshaft. The one or more conductors are coupled to the one or more transducers and extend along the driveshaft. The conductive shield is disposed around the one or more conductors. The shield-coupling capacitor is electrically coupled to the conductive shield and includes one or more rotating capacitors. The one or more rotating capacitors include one or more rotating plates and one or more stationary plates. The shield-coupling capacitor is configured and arranged for coupling to a system ground.

19 Claims, 7 Drawing Sheets

U.S. PATENT DOCUMENTS

| | | |
|---|---|---|
| 2007/0016054 A1 | 1/2007 | Cao et al. |
| 2007/0038111 A1 | 2/2007 | Rehrig et al. |
| 2007/0066900 A1 | 3/2007 | O'Keeffe |
| 2007/0083216 A1 | 4/2007 | Belef et al. |
| 2008/0051660 A1 | 2/2008 | Kakadaris et al. |
| 2008/0114254 A1 | 5/2008 | Matcovitch et al. |
| 2008/0146918 A1 | 6/2008 | Magnin et al. |

FOREIGN PATENT DOCUMENTS

| | | |
|---|---|---|
| EP | 1 475 040 A2 | 11/2004 |
| EP | 1 477 827 A1 | 11/2004 |
| EP | 1 142 316 B1 | 5/2005 |
| EP | 1 033 937 B1 | 8/2005 |
| EP | 1 032 309 B1 | 11/2005 |
| EP | 1 117 343 B1 | 10/2006 |
| EP | 1 021 129 B1 | 1/2008 |
| EP | 1 811 901 B1 | 4/2009 |
| WO | WO-99/15874 | 4/1999 |
| WO | WO-99/17660 | 4/1999 |
| WO | WO-9916347 | 4/1999 |
| WO | WO-99/23949 | 5/1999 |
| WO | WO-99/26541 | 6/1999 |
| WO | WO-00/19907 | 4/2000 |
| WO | WO-00/36826 | 6/2000 |
| WO | WO-0061008 | 10/2000 |
| WO | WO-02/02173 A1 | 1/2002 |
| WO | WO-03/011105 A3 | 2/2003 |
| WO | WO-2004/062502 A1 | 7/2004 |
| WO | WO-2006/015264 A2 | 2/2006 |
| WO | WO-2006/030408 A1 | 3/2006 |
| WO | WO-2006/086152 A2 | 8/2006 |
| WO | WO-2007/022133 A1 | 2/2007 |
| WO | WO-2007/040818 A1 | 4/2007 |
| WO | WO-2007/082218 A2 | 7/2007 |

* cited by examiner

SHIELDING FOR INTRAVASCULAR ULTRASOUND IMAGING SYSTEMS AND METHODS OF MAKING AND USING

CROSS REFERENCE TO RELATED APPLICATION

This application claims the benefit of U.S. Provisional Patent Application Ser. No. 61/050,616, filed on May 5, 2008, the entire contents of which is incorporated herein by reference.

TECHNICAL FIELD

The present invention is directed to the area of intravascular ultrasound imaging systems and methods of making and using the systems. The present invention is also directed to an intravascular ultrasound imaging system utilizing shielding for reducing electrical noise, as well as methods of making and using shielding and intravascular ultrasound system.

BACKGROUND

Intravascular ultrasound ("IVUS") imaging systems have proven diagnostic capabilities for a variety of diseases and disorders. For example, IVUS imaging systems have been used as an imaging modality for diagnosing blocked blood vessels and providing information to aid medical practitioners in selecting and placing stents and other devices to restore or increase blood flow. IVUS imaging systems have been used to diagnose atheromatous plaque build-up at particular locations within blood vessels. IVUS imaging systems can be used to determine the existence of an intravascular obstruction or stenosis, as well as the nature and degree of the obstruction or stenosis. IVUS imaging systems can be used to visualize segments of a vascular system that may be difficult to visualize using other intravascular imaging techniques, such as angiography, due to, for example, movement (e.g., a beating heart) or obstruction by one or more structures (e.g., one or more blood vessels not desired to be imaged). IVUS imaging systems can be used to monitor or assess ongoing intravascular treatments, such as angiography and stent placement in real (or almost real) time. Moreover, IVUS imaging systems can be used to monitor one or more heart chambers.

IVUS imaging systems have been developed to provide a diagnostic tool for visualizing a variety is diseases or disorders. An IVUS imaging system can include a control module (with a pulse generator, an image processor, and a monitor), a catheter, and one or more transducers disposed in the catheter. The transducer-containing catheter can be positioned in a lumen or cavity within, or in proximity to, a region to be imaged, such as a blood vessel wall or patient tissue in proximity to a blood vessel wall. The pulse generator in the control module generates electrical pulses that are delivered to the one or more transducers and transformed to acoustic pulses that are transmitted through patient tissue. Reflected pulses of the transmitted acoustic pulses are absorbed by the one or more transducers and transformed to electric pulses. The transformed electric pulses are delivered to the image processor and converted to an image displayable on the monitor.

BRIEF SUMMARY

In one embodiment, a catheter assembly for an intravascular ultrasound system includes a catheter, an imaging core, and a shield-coupling capacitor. The catheter has a longitudinal length, a distal end, and a proximal end. The catheter defines a lumen extending along the longitudinal length of the catheter from the proximal end to the distal end. The imaging core is configured and arranged for inserting into the lumen. The imaging core includes a rotatable driveshaft, one or more transducers, one or more conductors, and a conductive shield. The rotatable driveshaft has a distal end and a longitudinal length. The one or more transducers are mounted to the distal end of the rotatable driveshaft and are configured and arranged for transforming applied electrical pulses to acoustic pulses and also for transforming received echo pulses to electrical pulses. The one or more conductors are coupled to the one or more transducers and extend along the longitudinal length of the driveshaft. The conductive shield is disposed around the one or more conductors. The shield-coupling capacitor is electrically coupled to the conductive shield and includes one or more rotating capacitors. The one or more rotating capacitors include one or more rotating plates and one or more stationary plates. The shield-coupling capacitor is configured and arranged for coupling to a system ground.

In another embodiment, an intravascular ultrasound imaging system includes a catheter, an imaging core, a shield-coupling capacitor, and a control module. The catheter has a longitudinal length, a distal end, and a proximal end. The catheter defines a lumen extending along the longitudinal length of the catheter from the proximal end to the distal end. The imaging core is configured and arranged for inserting into the lumen. The imaging core includes a rotatable driveshaft, one or more transducers, one or more conductors, and a conductive shield. The rotatable driveshaft has a distal end and a longitudinal length. The one or more transducers are mounted to the distal end of the rotatable driveshaft and are configured and arranged for transforming applied electrical pulses to acoustic pulses and also for transforming received echo pulses to electrical pulses. The one or more conductors are coupled to the one or more transducers and extend along the longitudinal length of the driveshaft. The conductive shield is disposed around the one or more conductors. The shield-coupling capacitor is electrically coupled to the conductive shield and includes one or more rotating capacitors. The one or more rotating capacitors include one or more rotating plates and one or more stationary plates. The shield-coupling capacitor is configured and arranged for coupling to a system ground. The control module is coupled to the imaging core and includes a pulse generator and a processor. The pulse generator is configured and arranged for providing electric pulses to the one or more transducers. The processor is configured and arranged for processing received electrical pulses from the one or more transducers to form at least one image. The pulse generator and the processor are both electrically coupled to the one or more transducers via the one or more conductors.

In yet another embodiment, a method for imaging a patient using an intravascular ultrasound imaging system includes inserting a catheter into patient vasculature. The catheter includes an imaging core electrically coupled to a control module by one or more conductors. The imaging core is positioned in a region to be imaged. The control module transmits one or more electrical pulse to the imaging core. The imaging core receives one or more echo signals from a tissue-boundary between adjacent imaged patient tissues. The imaging core transmits one or more transformed echo signals to the control module for processing. Electric noise coupling the transformed echo signal(s) is shunted to a system ground via a shield-coupling capacitor that includes one or more rotating capacitors.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of intravascular ultrasound imaging systems and methods of making and using the systems. The present invention is also directed to an intravascular ultrasound imaging system utilizing shielding for reducing electrical noise, as well as methods of making and using shielding and intravascular ultrasound system.

Suitable intravascular ultrasound ("IVUS") imaging systems include, but are not limited to, one or more transducers disposed on a distal end of a catheter configured and arranged for percutaneous insertion into a patient. Examples of IVUS imaging systems with catheters are found in, for example, U.S. Pat. Nos. 7,306,561; and 6,945,938; as well as U.S. Patent Application Publication Nos. 20060253028; 20070016054; 20070038111; 20060173350; and 20060100522, all of which are incorporated by reference.

Figure 1:
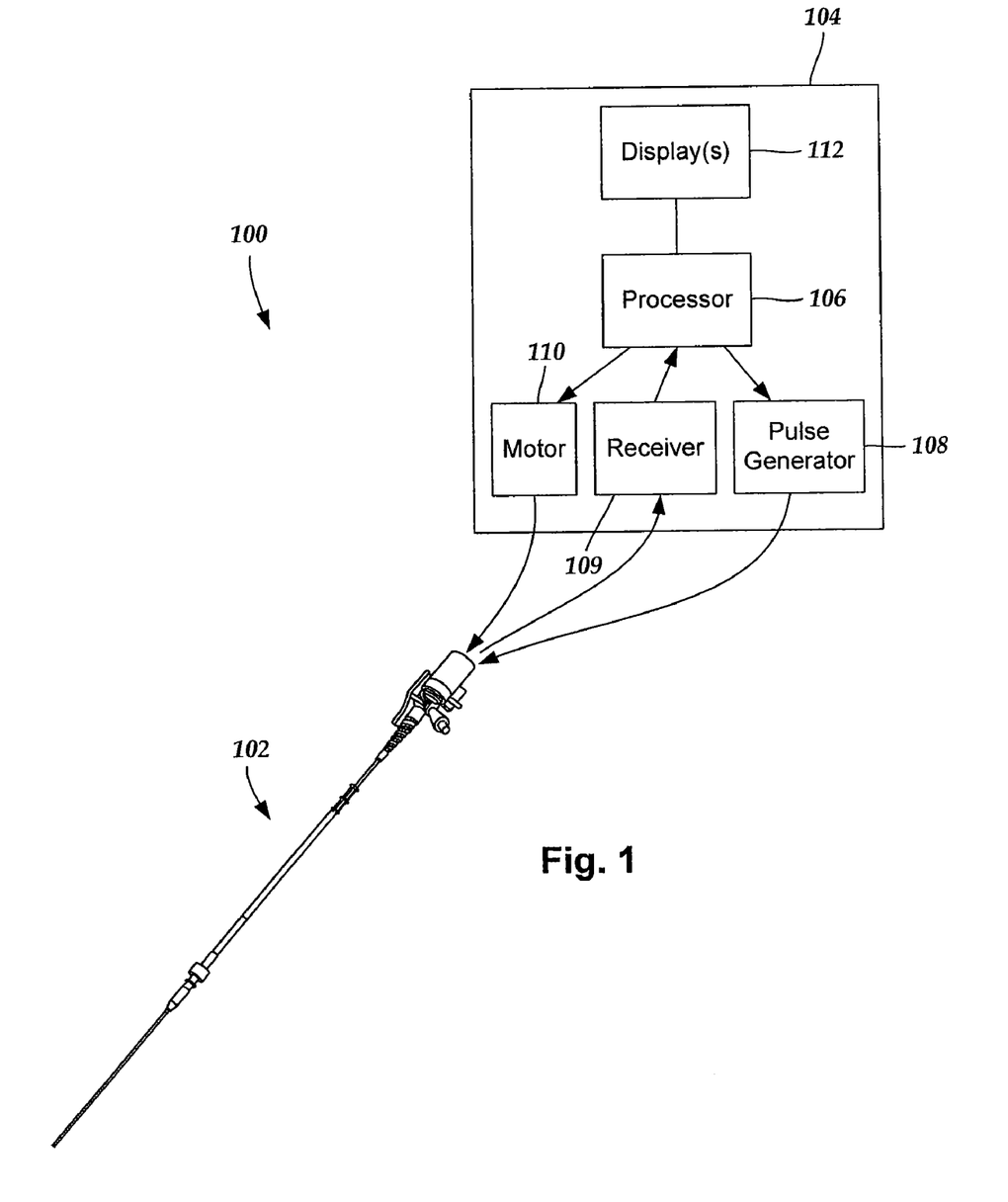
FIG. 1 is a schematic view of one embodiment of an intravascular ultrasound imaging system, according to the invention.

FIG. 1 illustrates schematically one embodiment of an IVUS imaging system 100. The IVUS imaging system 100 includes a catheter 102 that is coupleable to a control module 104. The control module 104 may include, for example, a processor 106, a pulse generator 108, a receiver 109, a motor 110, and one or more displays 112. In at least some embodiments, the pulse generator 108 forms electric pulses that may be input to one or more transducers (312 in FIG. 3) disposed in the catheter 102. In at least some embodiments, mechanical energy from the motor 110 may be used to drive an imaging core (306 in FIG. 3) disposed in the catheter 102. In at least some embodiments, electric pulses transmitted from the one or more transducers (312 in FIG. 3) may be input to the processor 106, via the receiver 109, for processing. In at least some embodiments, the processed electric pulses from the one or more transducers (312 in FIG. 3) may be displayed as one or more images on the one or more displays 112. In at least some embodiments, the processor 106 may also be used to control the functioning of one or more of the other components of the control module 104. For example, the processor 106 may be used to control at least one of the frequency or duration of the electrical pulses transmitted from the pulse generator 108, the gain of receiver 109, the rotation rate of the imaging core (306 in FIG. 3) by the motor 110, the velocity or length of the pullback of the imaging core (306 in FIG. 3) by the motor 110, or one or more properties of one or more images formed on the one or more displays 112.

Figure 2:
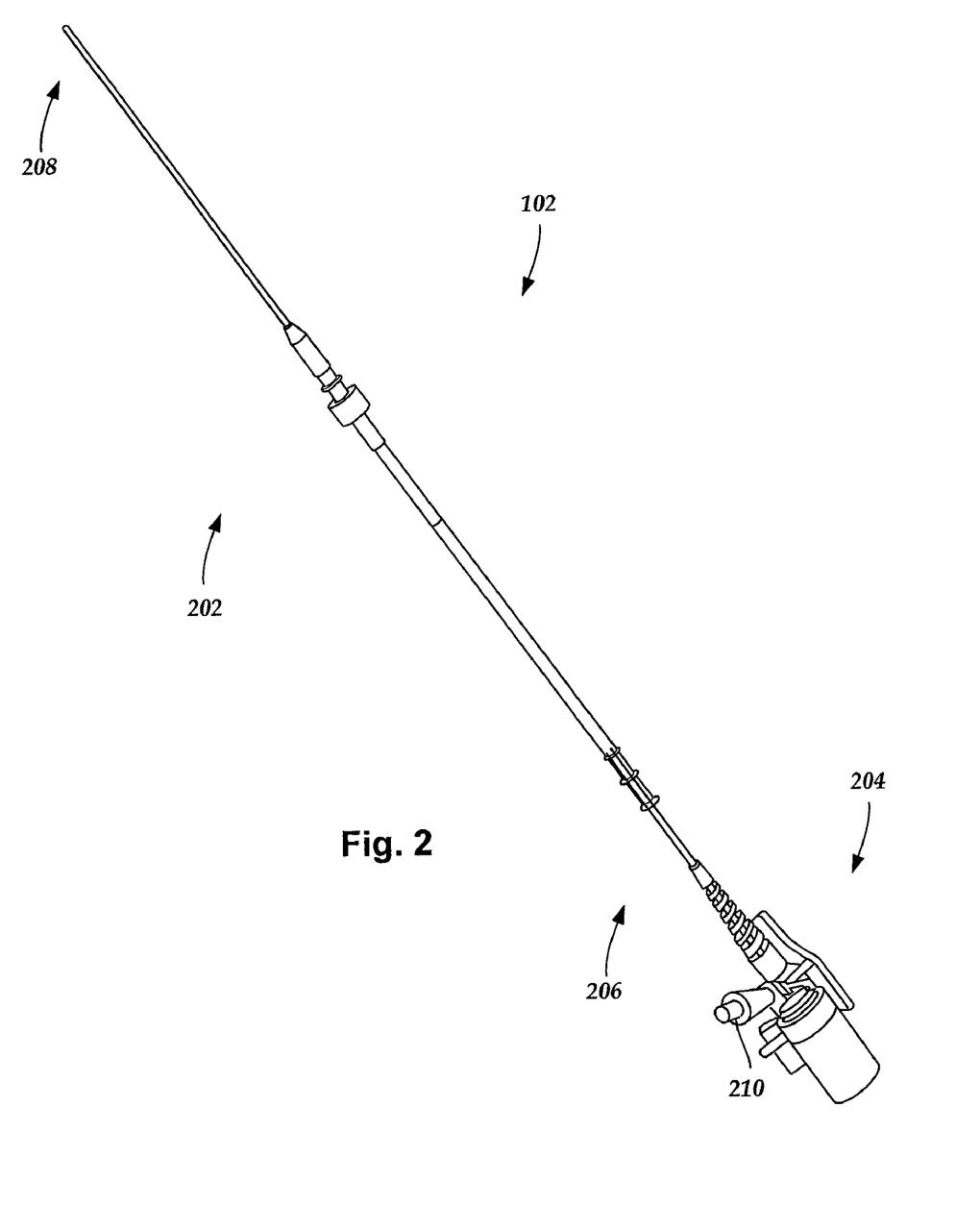
FIG. 2 is a schematic perspective view of one embodiment of a catheter of an intravascular ultrasound imaging system, according to the invention.

FIG. 2 is a schematic side view of one embodiment of the catheter 102 of the IVUS imaging system (100 in FIG. 1). The catheter 102 includes an elongated member 202 and a hub 204. The elongated member 202 includes a proximal end 206 and a distal end 208. In FIG. 2, the proximal end 206 of the elongated member 202 is coupled to the catheter hub 204 and the distal end 208 of the elongated member is configured and arranged for percutaneous insertion into a patient. In at least some embodiments, the catheter 102 defines at least one flush port, such as flush port 210. In at least some embodiments, the flush port 210 is defined in the hub 204. In at least some embodiments, the hub 204 is configured and arranged to couple to the control module (104 in FIG. 1). In some embodiments, the elongated member 202 and the hub 204 are formed as a unitary body. In other embodiments, the elongated member 202 and the catheter hub 204 are formed separately and subsequently assembled together.

Figure 3:
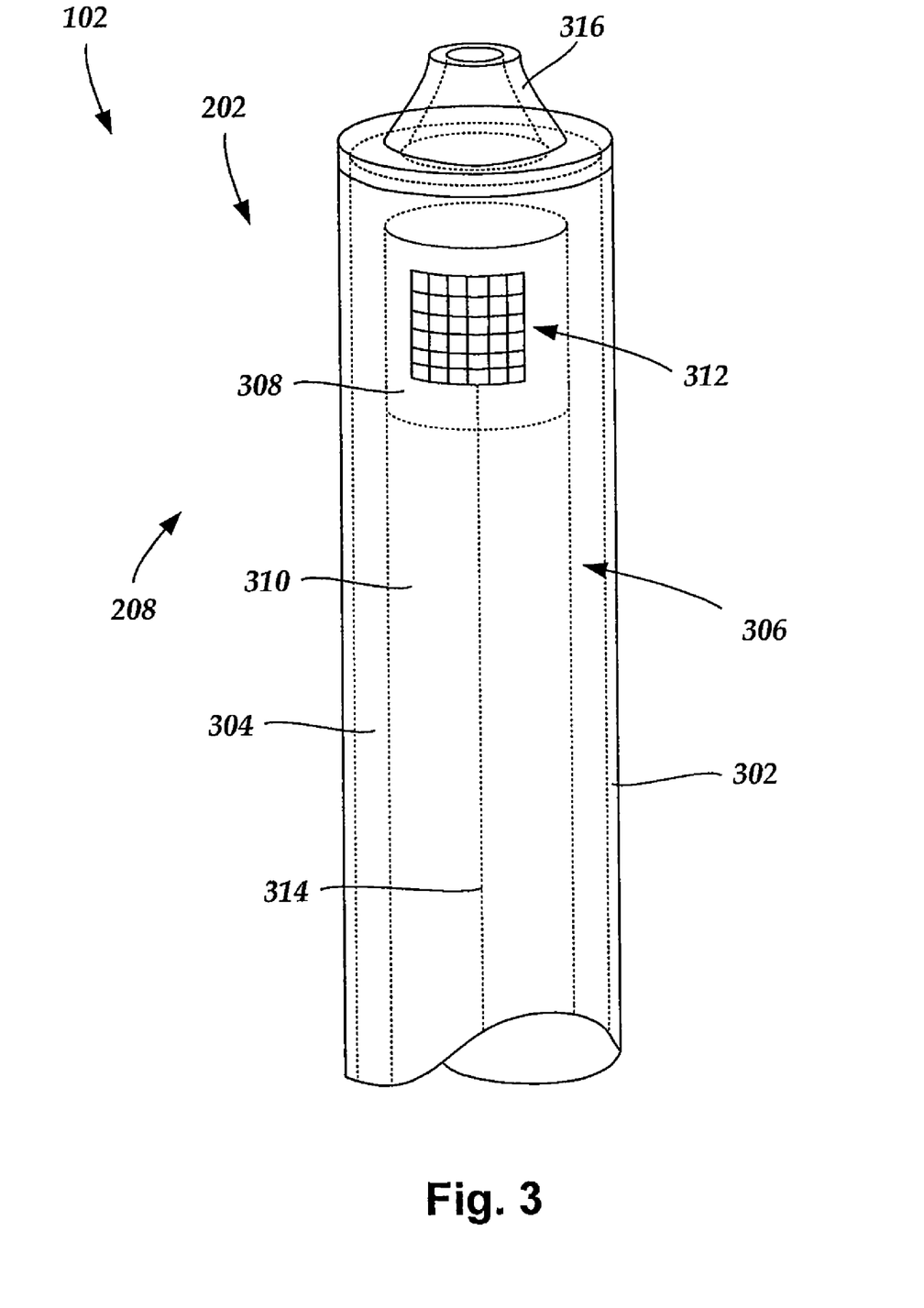
FIG. 3 is a schematic perspective view of one embodiment of a distal end of an elongated member of the catheter shown in FIG. 2 with an imaging core disposed in a lumen in the distal end of the elongated member, according to the invention.

FIG. 3 is a schematic perspective view of one embodiment of the distal end 208 of the elongated member 202 of the catheter 102. The elongated member 202 includes a sheath 302 and a lumen 304. An imaging core 306 is disposed in the lumen 304. The imaging core 306 includes an imaging device 308 coupled to a distal end of a rotatable driveshaft 310.

The sheath 302 may be formed from any flexible, biocompatible material suitable for insertion into a patient. Examples of suitable materials include, for example, polyethylene, polyurethane, plastic, polyetheretherketone (PEEK), polytetrafluoroethylene (PTFE), ethylenevinylacetate (EVA), spiral-cut stainless steel, nitinol hypotube, and the like or combinations thereof.

One or more transducers 312 may be mounted to the imaging device 308 and employed to transmit and receive acoustic pulses. In a preferred embodiment (as shown in FIG. 3), an array of transducers 312 are mounted to the imaging device 308. In other embodiments, a single transducer may be employed. In yet other embodiments, multiple transducers in an irregular-array may be employed. Any number of transducers 312 can be used. For example, there can be two, three, four, five, six, seven, eight, nine, ten, twelve, fifteen, sixteen, twenty, twenty-five, fifty, one hundred, five hundred, one thousand, or more transducers. As will be recognized, other numbers of transducers may also be used.

The one or more transducers 312 may be formed from one or more known materials capable of transforming applied electrical pulses to pressure distortions on the surface of the one or more transducers 312, and vice versa. Examples of suitable materials include piezoelectric ceramic materials, piezocomposite materials, piezoelectric plastics, barium titanates, lead titanates, lead zirconate titanates, lead magnesium niobate-lead titanates, lead metaniobates, polyvinylidenefluorides, and the like. Additionally, capacitive micromachined ultrasound transducers (CMUTs), or the like, may be used.

The pressure distortions on the surface of the one or more transducers 312 form acoustic pulses of a frequency based on the resonant frequencies of the one or more transducers 312. The resonant frequencies of the one or more transducers 312 may be affected by the size, shape, and material used to form the one or more transducers 312. The one or more transducers 312 may be formed in any shape suitable for positioning within the catheter 102 and for propagating acoustic pulses of a desired frequency in one or more selected directions. For example, transducers may be disc-shaped, block-shaped, rectangular-shaped, oval-shaped, ring-shaped, and the like. The one or more transducers may be formed in the desired shape by any process including, for example, dicing, dice and fill, machining, chemical etching, plasma etching, reactive ion etching, microfabrication, and the like.

As an example, each of the one or more transducers 312 may include a layer of piezoelectric material sandwiched between conductive layers. For example, the layers may comprise deposited metallic materials or a conductive acoustic lens and a conductive backing material formed from an acoustically absorbent material (e.g., an epoxy substrate with tungsten particles). During operation, the piezoelectric layer may be electrically excited by applying an alternating voltage across the conducting layers on opposing sides of the piezoelectric layer to cause the emission of acoustic pulses.

In at least some embodiments, the one or more transducers 312 can be used to form a radial cross-sectional image of a surrounding space. Thus, for example, when the one or more transducers 312 are disposed in the catheter 102 and inserted into a blood vessel of a patient, the one more transducers 312 may be used to form an image of the walls of the blood vessel and tissue surrounding the blood vessel.

In at least some embodiments, the imaging core 306 may be rotated about a longitudinal axis of the catheter 102. As the imaging core 306 rotates, the one or more transducers 312 emit acoustic pulses in different radial directions. When an emitted acoustic pulse with sufficient energy encounters one or more medium boundaries, such as one or more tissue boundaries, a portion of the emitted acoustic pulse is reflected back to the emitting transducer as an echo pulse. Each echo pulse that reaches a transducer with sufficient energy to be detected is transformed to an electrical signal in the receiving transducer. The one or more transformed electrical signals are transmitted to the control module (104 in FIG. 1) where the processor 106 processes the electrical-signal characteristics to form a displayable image of the imaged region based, at least in part, on a collection of information from each of the acoustic pulses transmitted and the echo pulses received. In at least some embodiments, the rotation of the imaging core 306 is driven by the motor 110 disposed in the control module (104 in FIG. 1).

As the one or more transducers 312 rotate about the longitudinal axis of the catheter 102 emitting acoustic pulses, a plurality of images are formed that collectively form a radial cross-sectional image of a portion of the region surrounding the one or more transducers 312, such as the walls of a blood vessel of interest and the tissue surrounding the blood vessel. In at least some embodiments, the radial cross-sectional image can be displayed on one or more displays 112.

In at least some embodiments, the imaging core 306 may also move longitudinally along the blood vessel within which the catheter 102 is inserted so that a plurality of cross-sectional images may be formed along a longitudinal length of the blood vessel. In at least some embodiments, during an imaging procedure the one or more transducers 312 may be retracted (i.e., pulled back) along the longitudinal length of the catheter 102. In at least some embodiments, the catheter 102 includes at least one telescoping section that can be retracted during pullback of the one or more transducers 312. In at least some embodiments, the motor 110 drives the pullback of the imaging core 306 within the catheter 102. In at least some embodiments, the motor 110 pullback distance of the imaging core is at least 5 cm. In at least some embodiments, the motor 110 pullback distance of the imaging core is at least 10 cm. In at least some embodiments, the motor 110 pullback distance of the imaging core is at least 15 cm. In at least some embodiments, the motor 110 pullback distance of the imaging core is at least 20 cm. In at least some embodiments, the motor 110 pullback distance of the imaging core is at least 25 cm.

The quality of an image produced at different depths from the one or more transducers 312 may be affected by one or more factors including, for example, bandwidth, transducer focus, beam pattern, as well as the frequency of the acoustic pulse. The frequency of the acoustic pulse output from the one or more transducers 312 may also affect the penetration depth of the acoustic pulse output from the one or more transducers 312. In general, as the frequency of an acoustic pulse is lowered, the depth of the penetration of the acoustic pulse within patient tissue increases. In at least some embodiments, the IVUS imaging system 100 operates within a frequency range of 5 MHz to 60 MHz.

In at least some embodiments, one or more conductors 314 electrically couple the transducers 312 to the control module 104 (See FIG. 1). In at least some embodiments, the one or more conductors 314 extend along a longitudinal length of the rotatable driveshaft 310.

In at least some embodiments, the catheter 102 with one or more transducers 312 mounted to the distal end 208 of the imaging core 308 may be inserted percutaneously into a patient via an accessible blood vessel, such as the femoral artery, at a site remote from the selected portion of the selected region, such as a blood vessel, to be imaged. The catheter 102 may then be advanced through the blood vessels of the patient to the selected imaging site, such as a portion of a selected blood vessel.

Ultrasound images formed by an IVUS imaging system may be degraded by electrical noise coupling with electrical signals transmitting between the one or more transducers 312 and the control module 104. Creation of electrical noise may be due to a capacitance between the catheter 102 and the body of a patient. One way to decrease electrical noise is by increasing the thickness of the insulating dielectric cover or increasing the space between the conductors 314 and the patient. However, it is generally desirable to use a small diameter elongated member 202 to increase the number of blood vessels that the one or more coupled transducers 312 may be able to image.

Another way to decrease electrical noise is by disposing a conductive shield within the catheter 102 and coupling the conductive shield to a system ground, such as a control-module-chassis ground. In at least some embodiments, the conductive shield is disposed over the driveshaft 310. The conductive shield may also be insulated from a patient by disposing a dielectric cover over the conductive shield. In at least some embodiments, the dielectric cover is the sheath 302. Unfortunately, when the conductive shield is coupled to a system ground, potentially harmful leakage currents may occur—especially during fault conditions in the control module 104 (or other electronic device). Consequently, safety standards, regulations, and guidelines have been developed limiting the level of allowable leakage current to which a patient may be exposed during normal operating conditions or during single-fault conditions. However, decreasing electrical noise by shunting the electrical noise to the system ground, while also providing patient safety from leakage current, may be difficult to achieve.

Decreasing electrical noise, while also providing patient safety from leakage current, may additionally be complicated by some IVUS imaging system designs. Some IVUS imaging system designs employ a rotating barrier and a high-voltage barrier. In at least some embodiments, the IVUS imaging system 100 utilizes a partially-rotating transformer ("rotating transformer") electrically coupled to one or more rotating transducers. In at least some embodiments, the rotating transformer includes a stationary primary winding and a rotating secondary winding coupled to the driveshaft 310 that rotates with the one or more transducers 312. In at least some embodiments, the IVUS imaging system 100 also utilizes a high-voltage isolation transformer along the electrical path to protect a patient from potentially dangerous leakage currents that may arise from a system fault.

In at least some embodiments, a shield-coupling capacitor couples a conductive shield to a system ground. In at least some embodiments, the capacitive shielding system can cross both a rotating barrier and a high-voltage barrier. In at least some embodiments, the shield-coupling capacitor may reduce electrical noise in one or more frequencies. In at least some embodiments, the shield-coupling capacitor may decrease patient leakage-current exposure.

Figure 4A:
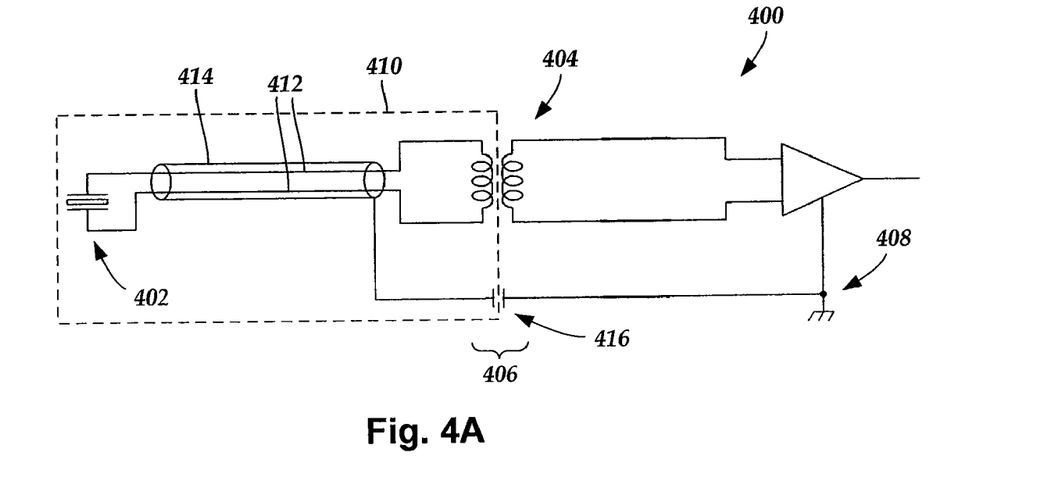
FIG. 4A is a schematic diagram of one embodiment of an imaging circuit for a catheter of an intravascular ultrasound imaging system with a shield-coupling capacitor, the shield-coupling capacitor including a rotating capacitor, according to the invention.

FIG. 4A is a schematic diagram of one embodiment of an imaging circuit 400. In at least some embodiments, the imaging circuit 400 may be implemented in the catheter (102 of FIG. 1) of the IVUS imaging system (100 of FIG. 1). The imaging circuit 400 includes one or more transducers 402, a rotating transformer 404, a shield-coupling capacitor 406, and a system ground 408. In at least some embodiments, the catheter (102 in FIG. 1) includes a rotating distal end 410, shown in FIG. 4A and in subsequent figures as a dashed box. The rotating distal end 410 includes one or more rotating transducers 402 coupled to a rotating transformer 404 via one or more conductors 412 disposed in a conductive shield 414.

In at least some embodiments, the conductors 412 may include one or more shielded electrical cables, such as a coaxial cable, a twisted pair cable, or the like. In at least some embodiments, the conductive shield 414 may be coupled to the system ground 408 via the shield-coupling capacitor 406. In some embodiments, the conductive shield 414 is disposed around one or more of the conductors 412. In at least some embodiments, the conductive shield 414 is disposed inside the rotatable driveshaft (310 in FIG. 3).

The shield-coupling capacitor 406 includes a rotating capacitor 416. In at least some embodiments, the rotating capacitor 416 has a capacitance selected to provide a low impedance path for radio-frequency currents to follow from the conductive shield 414 to the system ground 408 while also maintaining a desired breakdown voltage. In at least some embodiments, the shield-coupling capacitor 406 may also include one or more capacitors (or other electronic components) in series with the rotating capacitor 416. In at least some embodiments, at least one of the capacitors in series is a high-voltage capacitor.

Figure 4B:
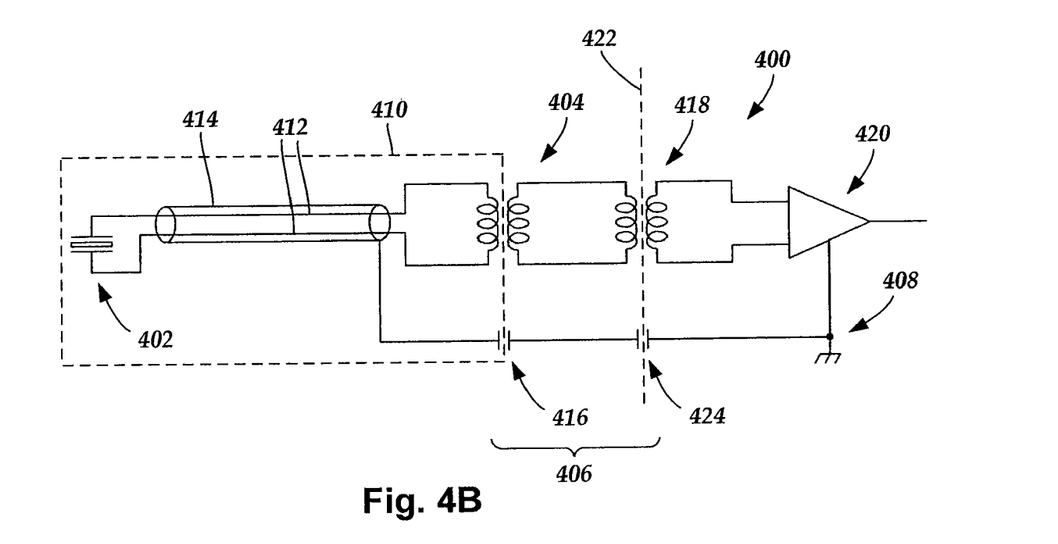
FIG. 4B is a schematic diagram of one embodiment of an imaging circuit for a catheter of an intravascular ultrasound imaging system with a shield-coupling capacitor, the shield-coupling capacitor including a rotating capacitor in series with a high-voltage capacitor, according to the invention.

FIG. 4B is a schematic diagram of another embodiment of the imaging circuit 400. In FIG. 4B, the imaging circuit 400 includes the one or more transducers 402, the rotating transformer 404, the shield-coupling capacitor 406, the system ground 408, and the rotating distal end 410. Additionally, the imaging circuit 400 includes a high-voltage isolation transformer 418 and at least one amplifier, such as amplifier 420. The rotating distal end 410 includes the one or more rotating transducers 402 coupled to the rotating transformer 404 via one or more conductors 412 disposed in the conductive shield 414. In at least some embodiments, the conductive shield 414 may be coupled to the system ground 408 via the shield-coupling capacitor 406. In FIG. 4B, a high-voltage barrier is represented by a dashed vertical line 422 extending between windings of the high-voltage transformer 418.

In at least some embodiments, the shield-coupling capacitor 406 includes one or more rotating capacitors 416 placed in series with one or more high-voltage capacitors 424 to maintain high-voltage isolation. In at least some embodiments, the series combination of the one or more rotating capacitors 416 and the one or more high-voltage capacitors 424 provides a low impedance path for radio-frequency currents from the conductive shield 414 to follow to the system ground 408 while also maintaining a desired breakdown voltage.

The leakage current may be related to the capacitance and, in some cases, may be proportional to the capacitance. Thus, when the shield-coupling capacitor 406 includes two or more capacitors in series, such as the capacitors 416 and 424, the capacitors may be selected so that the series capacitance reduces leakage current. In at least some embodiments, the capacitances of each of the capacitors 416 and 424 may be selected so that the conductive shield 414 may be coupled to the system ground 408 without exposing a patient to leakage current above a selected level during normal operation of the IVUS imaging system (100 in FIG. 1) or a system fault. In at least some embodiments, the capacitances of each of the capacitors 416 and 424 are chosen to that the levels of potential leakage current that a patient may be exposed to during a system fault does not exceed a level determined by one or more industry standards or safety regulations or guidelines. In one particular embodiment, the capacitances of the capacitors 416 and 424 are chosen to limit patient leakage current to a maximum 10 µA RMS under normal conditions or 50 µA RMS under single fault conditions, as currently required by Underwriters Laboratories, under UL 2601-1, for type CF devices (those medical devices with applied parts in direct conductive contact with a patient heart).

An estimated series capacitance needed in order to not exceed a given leakage current, for example, the maximum patient leakage current of 10 µA RMS under normal conditions (under UL 2601-1), may be obtained using known voltages and frequencies. In at least some embodiments, the IVUS imaging system (100 in FIG. 1) operates at 240 V at 60 Hz. Adding a 10% safety margin to 240 V is 264 V. In at least some embodiments, the maximum patient leakage current of 10 µA RMS under normal conditions (under UL 2601-1) at 60 Hz (and using a voltage of 240 V+10%=264 V) is obtained through a capacitance of 100 pF. Thus, the series combination of the capacitors 416 and 424 may be set at a capacitance so that the leakage current does not exceed a given level. For example, the capacitors 416 and 424 may be selected to have a series capacitance below 100 pF in order to not exceed a maximum patient leakage current of 10 µA RMS under normal conditions. For example, in at least some embodiments the capacitances of the capacitors 416 and 424 are selected such that the series capacitance is less than 100 pF, such as 90 pF.

Likewise, the capacitances of the capacitors 416 and 424 can be selected such that when either of the two capacitors 416 and 424 is short-circuited, the leakage current to which the patient is exposed does not exceed a predetermined value. For example, in at least some embodiments, the series capacitance of the capacitors 416 and 424 may be set so that, when either one of the capacitors 416 and 424 is short-circuited, the leakage current to which the patient is exposed does not exceed a predetermined safety level, such as 50 µA RMS (as currently required by Underwriters Laboratories, under UL 2601-1). In at least some embodiments, when it is desired to not exceed a single fault leakage current of 50 µA RMS, each of the capacitors 416 and 424 may be set to not exceed 400 pF. For example, in one example, when the capacitance of the rotating capacitor 416 is 300 pF and the capacitance of the high-voltage capacitor 424 is 129 pF, the normal operating leakage current is approximately 9 µA RMS. A short-circuit of the rotating capacitor 416 may result in a leakage current of approximately 13 µA RMS. Similarly, a short-circuit of the high-voltage capacitor 424 may result in a leakage current of approximately 30 µA RMS.

Thus, the capacitors 416 and 424 may be placed in series to shunt noise signals to the system ground 408 in order to decrease electrical noise, while not exposing a patient to undue risk from leakage current under normal operating condition of the IVUS imaging system (100 in FIG. 1) or under single-fault conditions. In the example provided, placing the rotating capacitor 416 and the high-voltage capacitor 424 in series and setting one of the two capacitors 416 and 424 at 300 pF and the other of the two capacitors 416 and 424 at 129 pF results in a current leakage during normal operating conditions that is below the maximum allowable level as set by the current safety standard of UL 2601-1. Additionally, a short-circuit of either of the two capacitors 416 and 424 with the abovementioned capacitances results in single-fault leakage current that is below the maximum allowable level as set by the current safety standard of UL 2601-1.

In at least some embodiments, the rotating capacitor 416 includes concentric cylindrical plates, with at least one of the plates rotating with the rotating distal end 410. In at least some embodiments, one or more dielectric materials may be disposed between the plates. In at least some embodiments, the dielectric is air. In other embodiments, at least a portion of the space between the plates may be filled with one or more dielectrics, such as one or more plastics, synthetic fluoropolymers, or the like or combinations thereof. In some embodiments, the rotating capacitor 416 may be formed as a single unit.

In at least some preferred embodiments, the rotating capacitor 416 may be multi-sectional. For example, the rotating capacitor 416 may be split so that one or more sections are positioned on either end of the rotating transformer 404. In other embodiments, one or more rotating capacitors 416, or one or more sections of a single rotating capacitor 416, are disposed on one side of the rotating transformer 404. In a preferred embodiment, the rotating capacitor 416 is mechanically coupled to the rotating transformer 404. For example, the rotating capacitor 416 may include at least one concentric cylindrical plate mechanically coupled to a frame and at least one concentric cylindrical plate mechanically coupled to the rotor of the rotating transformer 404. For example, a rotating plate of the rotating capacitor 416 may be coupled to the rotor of the rotating transformer 404 and a stationary plate of the rotating capacitor 416 may be coupled to a stationary portion of the frame of the rotating transformer 404, such as a stator.

Figure 5A:
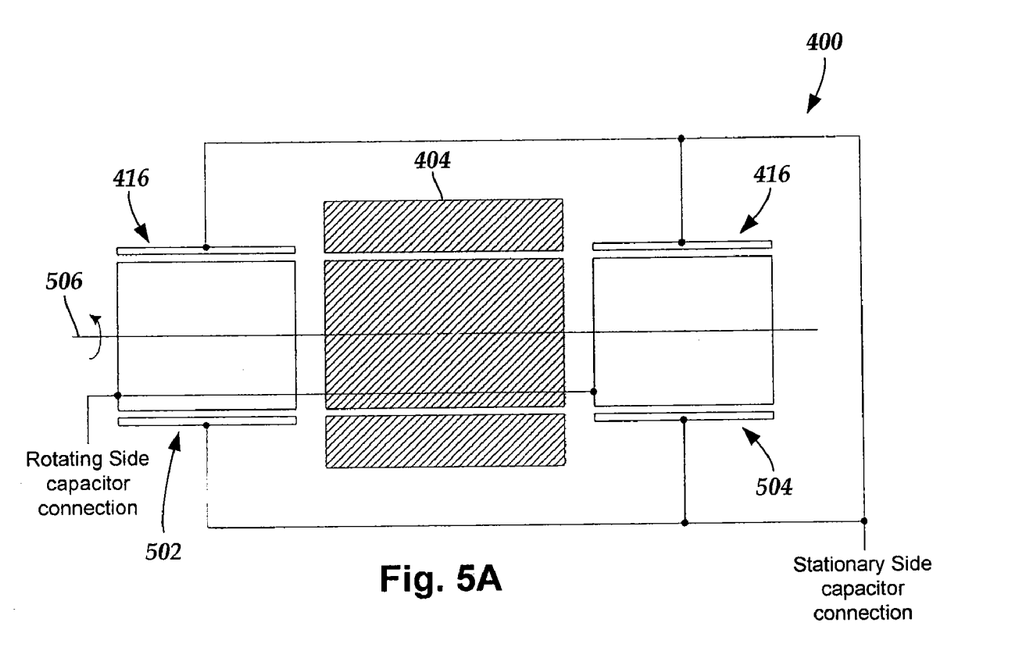
FIG. 5A is a schematic diagram of one embodiment of a portion of an imaging circuit for a catheter of an intravascular ultrasound imaging system with a shield-coupling capacitor, the portion of the imaging circuit including a rotating capacitor and a rotating transformer, according to the invention.

FIG. 5A is a schematic diagram of one embodiment of a portion of the imaging circuit 400 for the catheter (102 in FIG. 1) of the IVUS imaging system (100 in FIG. 1). The portion of the imaging circuit 400 includes the rotating transformer 404 and the rotating capacitor 416. In FIG. 5A, the rotating capacitor 416 includes two sections 502 and 504 flanking the rotating transformer 404. Line 506 shows an exemplary axis of rotation for the rotating portion of the catheter (102 in FIG. 1).

Figure 5B:
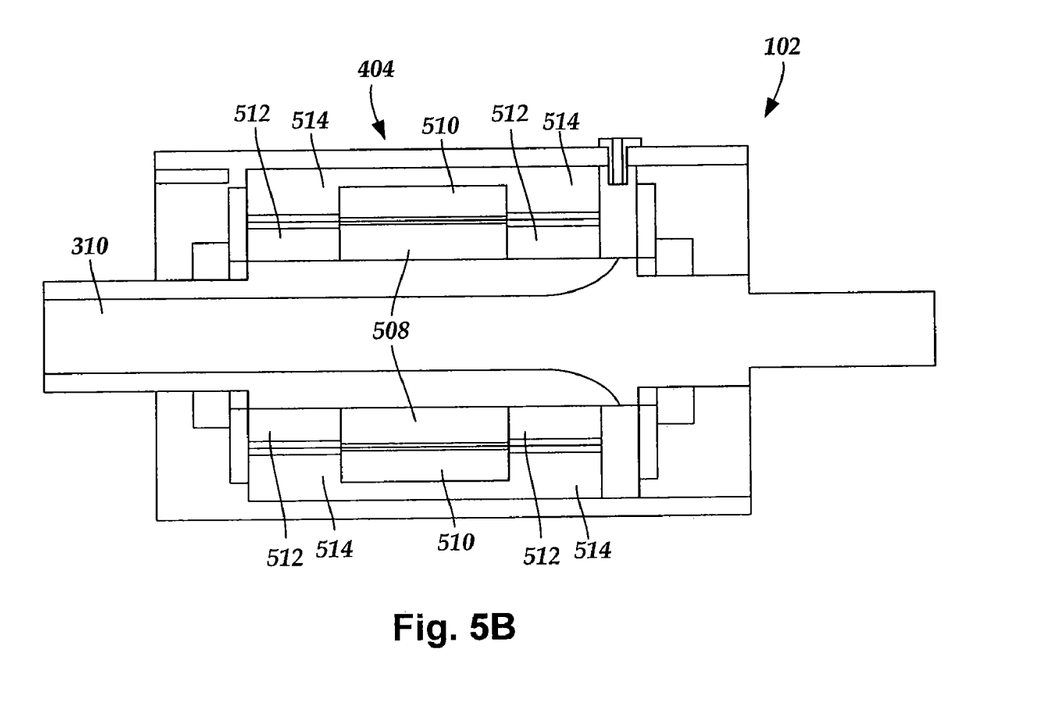
FIG. 5B is a schematic longitudinal cross-sectional view of one embodiment of the rotating capacitor shown in FIG. 5A and the rotating transformer in a catheter of an intravascular ultrasound imaging system with a shield-coupling capacitor, according to the invention.

FIG. 5B is a schematic longitudinal cross-sectional view of one embodiment of the two sections 502 and 504 of the rotating capacitor 416 flanking the rotating transformer 404 coupled to the driveshaft 310. In FIG. 5B, a rotating secondary winding 508 of the rotating transformer 404 is coupled to the rotating driveshaft 310 and a stationary primary winding 510 is positioned lateral to the rotating secondary winding 508. Each of the two sections 502 and 504 includes a rotating plate 512 coupled to the rotating driveshaft 310 and a stationary plate 514 positioned lateral to the rotating plate 512. In at least some embodiments, the rotating plates 512 are coupled to the rotor of the rotating transformer 404. In at least some embodiments, the stationary plate 514 is coupled to the stator of the rotating transformer 404.

Figure 5C:
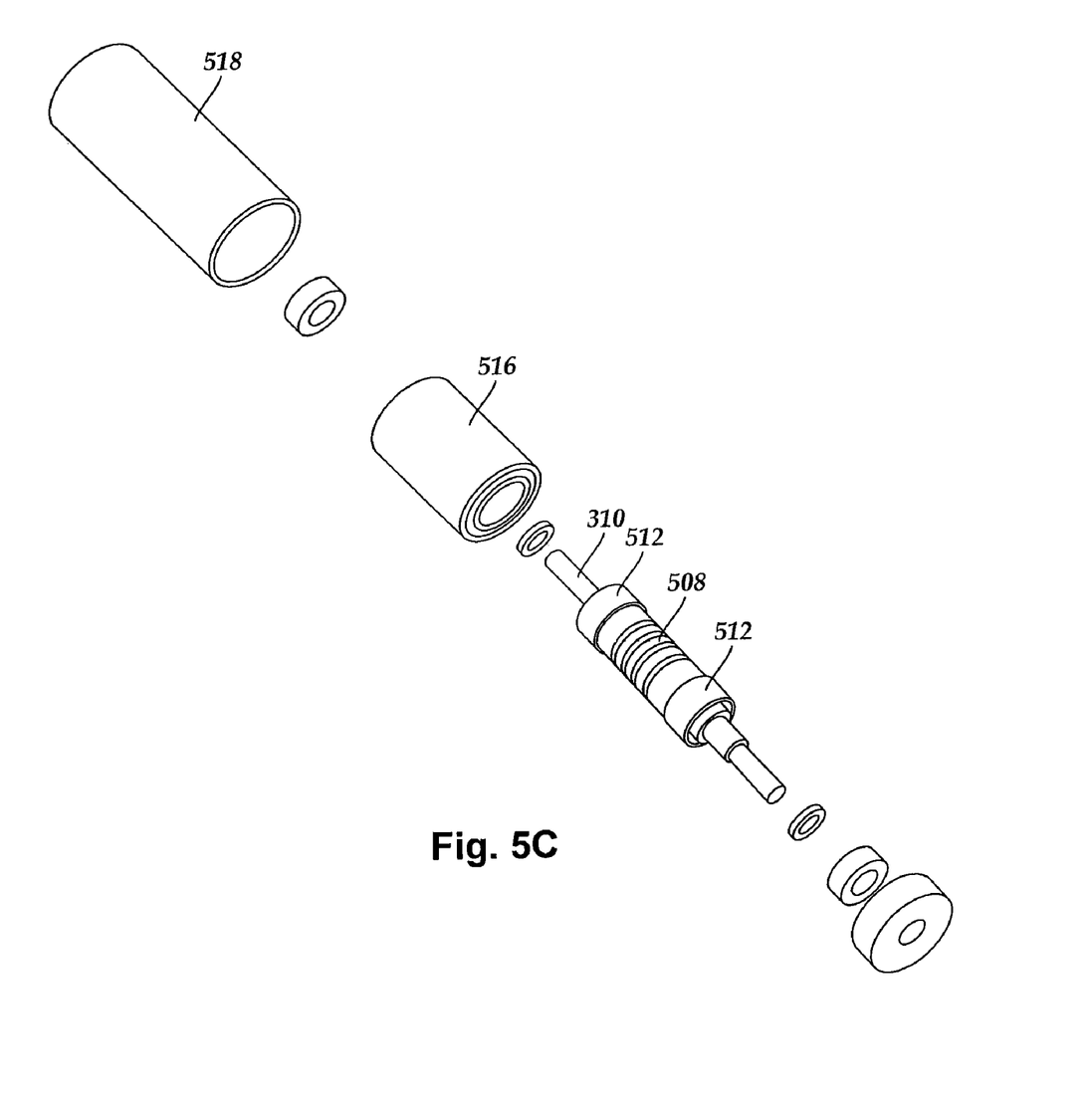
FIG. 5C is a schematic exploded perspective view of one embodiment of the rotating capacitor shown in FIG. 5B and the rotating transformer coupled to a driveshaft configured and arranged for insertion into a catheter of an intravascular ultrasound imaging system with a shield-coupling capacitor, according to the invention.

FIG. 5C is an exploded perspective view of one embodiment of the rotating secondary winding 508 and two flanking rotating plates 512 coupled to the rotating driveshaft 310. In FIG. 5C, the stationary primary winding 510 and flanking stationary plates 514 are shown as a single piece 516. In at least some embodiments, a conductive shield 518 is configured and arranged to be disposed over the stationary primary winding 510 and the stationary plates 514.

In at least some embodiments, the shield-coupling capacitor 406 is designed to decrease impedance at one or more frequencies corresponding to the one or more frequencies of interfering electrical noise. In at least some embodiments, the IVUS imaging system 100 operates within a frequency range of 5 MHz to 60 MHz. Under certain conditions, the magnitude of the impedance of a 90 pF capacitor is approximately 354Ω at 5 MHz and 30Ω at 30 MHz. It has been shown experimentally that an impedance range of 30Ω to 354Ω (especially towards the high end of the frequency range) is useful for enhancing the performance of a shield-coupling capacitor 406.

When the rotating capacitor 416 is split into two or more parts, such as the two parts 502 and 504, the combined capacitance of the two or more parts may be estimated using the following formula:

$$C = (\epsilon_0 \epsilon_R 2\pi R \, l)/d;$$

where C is the net capacitance of each part, such as the parts 502 and 504, $\epsilon_0$ is the free space dielectric constant, $\in_R$ is the relative dielectric constant (in at least some embodiments, $\in_R=1.0$ for air), R is the mean of the rotor outside radius and the stator inside radius, l is the sum of the lengths of all the individual capacitor plates (such as rotating plates 512 and stationary plates 514 of FIG. 5B), and d is the gap distance between the rotor and the stator.

Using the above formula, it can be determined how to adjust various parameters (such as the sum of the lengths of all the individual capacitor plates, the thickness of the gap between the rotor and stator, and the like or combinations thereof) in order to obtain a net capacitance for the rotating capacitor 416 that, when placed in series with the high-voltage capacitor 424, enhances capacitive shielding performance. In at least some embodiments, system performance is enhanced by decreasing electrical noise. In at least some embodiments, electrical noise is decreased by shunting electrical noise to the system ground 408. As an example of parameter adjustments, when each of the two parts 502 and 504 is approximately 0.5 inches (1.27 cm) in length, and when the rotor outside diameter is approximately 0.5 inches (1.27 cm), and when the gap between the rotor and stator is approximately 0.002 inches (0.005 cm), then the net capacitance is approximately 180 pF. A net capacitance of 180 pF for the rotating capacitor 416, when placed in series with the high-voltage capacitor 424, may enhance shield performance.

Figure 6:
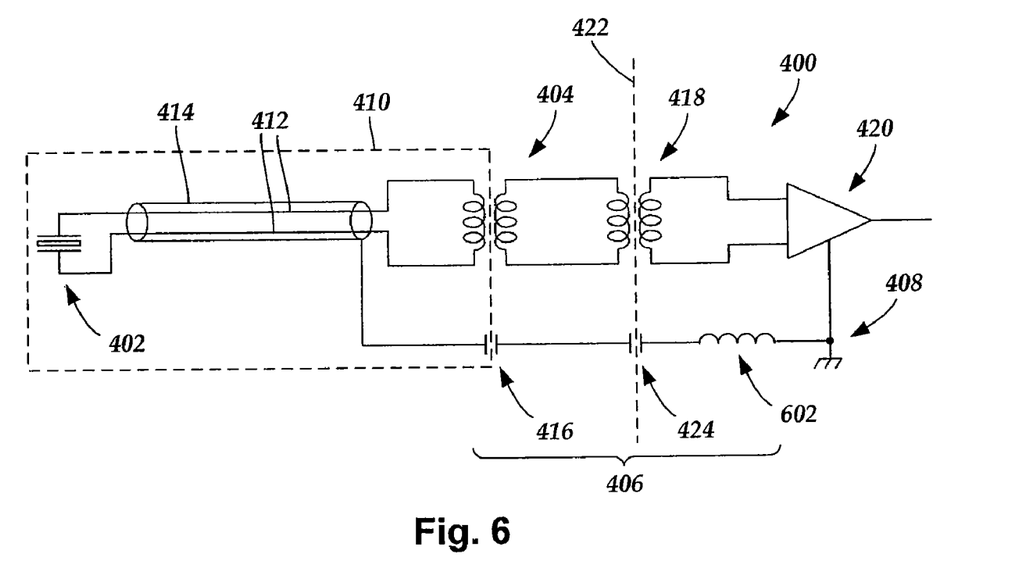
FIG. 6 is a schematic diagram of one embodiment of an imaging circuit for a catheter of an intravascular ultrasound imaging system with a shield-coupling capacitor, the shield-coupling capacitor including a rotating capacitor and a high-voltage capacitor in series with an inductor, according to the invention.

In at least some embodiments, the shield-coupling capacitor 406 may further include an inductor. FIG. 6 is a schematic circuit diagram of one embodiment of the imaging circuit 400 for the catheter (102 in FIG. 1) of the intravascular ultrasound imaging system (100 in FIG. 1). The imaging circuit 400 includes one or more transducers 402, the rotating transformer 404, the high-voltage transformer 418, the shield-coupling capacitor 406, and the system ground 408. In at least some embodiments, the catheter (102 in FIG. 1) includes the rotating distal end 410, shown in FIG. 6 as a dashed box. The rotating distal end 410 includes the one or more transducers 402 coupled to the rotating transformer 404 by one or more conductors 412 disposed in the conductive shield 414. In FIG. 6, the high-voltage isolation barrier is represented by the dashed vertical line 422 extending between windings of the high-voltage transformer 418. In at least some embodiments, the imaging circuit 400 also includes at least one amplifier, such as amplifier 420. In at least some embodiments, the conductive shield 414 is coupled to the system ground 408 via the at least one amplifier 420.

The shield-coupling capacitor 406 includes an inductor 602 placed in series with the one or more rotating capacitors 416 and the one or more high-voltage capacitors 424 to maintain high-voltage isolation. In at least some embodiments, the series combination of the inductor 602, the one or more rotating capacitors 416, and the one or more high-voltage capacitors 424 provides a low impedance path for radio-frequency currents from the conductive shield 414 and the conductors 412 to follow to the system ground 408 while also maintaining a desired breakdown voltage.

In at least some embodiments, placing the inductor 602 in series with the rotating capacitor 416 and the high-voltage capacitor 424 decreases the impedance of the shield-coupling capacitor 406 within a given frequency range around a resonant frequency of the imaging circuit 400. In other words, placement of the inductor 602 in series with the rotating capacitor 416 and the high-voltage capacitor 424 forms a bandpass filter (or a notch filter). For example, when the net capacitance of the rotating capacitor 416 and the high-voltage capacitor 424 is approximately 90 pF, then placing the inductor 602, with a 176 nH inductance, in series with the capacitors 416 and 424 may cause a decrease in the impedance of the net shield connection impedance in a frequency range in proximity to 40 MHz. Accordingly, electronic noise may be decreased in proximity to the same frequency range. In some embodiments, the inductor 602 may be a discrete component, and may be physically placed in either the catheter (102 in FIG. 1) or the control module (104 in FIG. 1) or a combination of the two locations. In other embodiments, the inductor 602 may be formed by adjusting the loop area of the conductors providing the conductive-shield connection.

Figure 7:
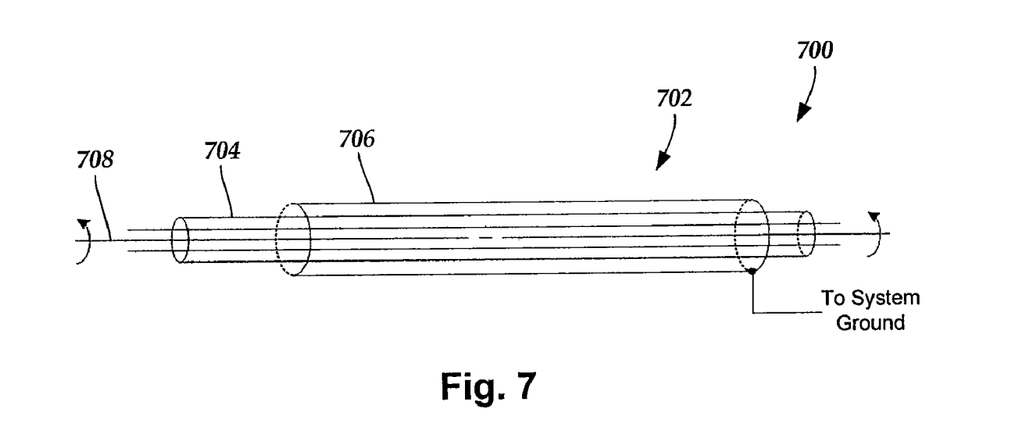
FIG. 7 is a schematic perspective view of one embodiment of a shield-coupling capacitor for a catheter of an intravascular ultrasound imaging system, the shield-coupling capacitor including a capacitor with a first plate and a second plate, the first plate including a rotating shield surrounding a driveshaft and the second plate including the stationary sheath with a shield-coupling capacitor disposed around the rotating shield, according to the invention.

In at least some embodiments, the shield-coupling capacitor 406 includes one or more rotating capacitors utilizing a rotating conductive shield, such as the conductive shield 414, and a stationary outer shield, such as the sheath 302, that includes a conductive shielding. FIG. 7 is a schematic perspective view of one embodiment of a capacitive shield 700. The capacitive shield 700 includes a rotating capacitor 702 with a first plate 704 and a second plate 706. In at least some embodiments, the first plate 704 is a rotating conductive shield (such as the conductive shield 414) and the second plate is a stationary sheath with a conductive shielding. In at least some embodiments, the first plate 704 rotates about an axis 708 of rotation. In at least some embodiments, the second plate 704 is coupled to the system ground 408. In at least some embodiments, the inductor 602 may be placed in series with the rotating capacitor 702 to reduce impedance on or around a selected frequency range.

In at least some embodiments, one or more selections or adjustments may be made so that the capacitance of the shield-coupling capacitor 406 (or the capacitive shield 700) falls within a desired range. Many adjustments may be possible including, for example, placing one or more dielectrics between the first plate 704 and the second plate 706, adjusting the types of dielectrics placed between the first plate 704 and the second plate 706 in order to change the dielectric constant, adjusting the thickness of the gap between the first plate 704 and the second plate 706, adjusting the length of the first plate 704 and the second plate 706, adjusting the surface area of one or more of the first plate 704 or the second plate 706, and the like or combinations thereof.

In at least some embodiments, at least a portion of the space between the first plate 704 and the second plate 706 may be at least partially filled with one or more dielectrics of a selected dielectric constant. For example, in some embodiments at least a portion of the space between the first plate 704 and the second plate 706 may be filled with one or more dielectrics with a dielectric constant of 2, such as one or more plastics, synthetic fluoropolymers, or the like or combinations thereof. The plates, however, should still allow for rotation of one plate relative to the other. In at least some embodiments, the surface area of one or more of the first plate 704 or the second plate 706 may be changed in many different ways including, for example, shortening the length of the rotating capacitor 702, limiting the length of one of the plates (preferably, the second plate 706) or at least limiting the conductive length of that plate, using conductive braid as a portion of one or both plates in order to reduce surface area, and the like or combinations thereof.

As an example of selecting or adjusting the capacitance, when the first plate 704 has an outer diameter of 0.110 inches (0.280 cm) and the second plate 706 has an inner diameter of 0.135 inches (0.343 cm) and the space between the first plate 704 and the second plate 706 is filled with air, the capacitance may be approximately 270 pF. However, when the space between the first plate 704 and the second plate 706 is filled with one or more materials with a dielectric constant of approximately 2, the capacitance may increase to approximately 540 pF. When the space between the first plate 704 and the second plate is partially filled with one or more materials with a dielectric constant of approximately 2, the capacitance may fall somewhere between 270 pF and 540 pF. When a lower capacitance is desired, the capacitance may be decreased, for example, by decreasing the surface area of one or more of the first plate 704 or the second plate 706, or by increasing the gap between the first plate 704 and the second plate 706, or both, or by decreasing the length of the first plate 704 or the second plate 706, or both.

In at least some embodiments, the shield-coupling capacitor 406 may be used in conjunction with one or more additional safety devices to further promote patient safety by decreasing potential patient exposure to leakage current. For example, in at least some embodiments a detector element may be positioned in series with the shield-coupling capacitor 406, the detector element triggering a current limiter, a latching switch, or the like to limit the amplitude of current flowing between a patient and a catheter to levels below a predetermined level. This arrangement may allow the shield-coupling capacitor 406 to be designed to a higher value to provide increased shielding effectiveness.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A catheter assembly for an intravascular ultrasound system, the catheter assembly comprising:
    a catheter having a longitudinal length, a distal end, and a proximal end, the catheter comprising a lumen extending along the longitudinal length of the catheter from the proximal end to the distal end;
    an imaging core configured and arranged for inserting into the lumen, the imaging core comprising
        a rotatable driveshaft having a distal end and a longitudinal length,
        at least one transducer mounted to the distal end of the rotatable driveshaft, the at least one transducer configured and arranged for transforming applied electrical pulses to acoustic pulses and also for transforming received echo pulses to electrical pulses,
        at least two conductors coupled to the at least one transducer and forming an electrical path to and from the at least one transducer, the at least two conductors extending along the longitudinal length of the driveshaft, and
        a conductive shield disposed around a portion of each of the at least two conductors; and
    a shield-coupling capacitor electrically coupled to the conductive shield, the shield-coupling capacitor comprising at least one rotating capacitor, the at least one rotating capacitor comprising at least one rotating plate and at least one stationary plate, the shield-coupling capacitor configured and arranged for coupling the conductive shield to a system ground.

2. The catheter assembly of claim 1, further comprising a rotatable transformer electrically coupled to the at least two conductors and separate from the at least one rotating capacitor, the rotatable transformer comprising at least one rotatable winding, the at least one transducer, the at least two conductors, and the rotatable winding of the rotatable transformer defining a loop.

3. The catheter assembly of claim 1, further comprising a high-voltage isolation transformer in electrical contact with the at least two conductors and separate from the rotating capacitor.

4. The catheter assembly of claim 1, wherein the shield-coupling capacitor further comprises at least one high-voltage capacitor in series with the rotating capacitor.

5. The catheter assembly of claim 4, wherein the shield-coupling capacitor further comprises at least one inductor in series with the at least one high-voltage capacitor and the at least one rotating capacitor.

6. The catheter assembly of claim 2, wherein the rotating transformer further comprises a rotatable rotor and a stationary stator.

7. The catheter assembly of claim 6, wherein at least one of the rotating plates of the at least one rotating capacitor is mechanically coupled to the rotatable rotor and at least one of the stationary plates of the at least one rotating capacitor is mechanically coupled to the stationary stator.

8. The catheter assembly of claim 2, wherein the at least one rotating capacitor is split into at least two sections, each of the at least two sections comprising at least one rotating plate and at least one stationary plate.

9. The catheter assembly of claim 1, wherein the shield-coupling capacitor further comprises at least one detector element.

10. The catheter assembly of claim 1, wherein a plate of the at least one rotating capacitor comprises at least a portion of the conductive shield disposed around the rotatable driveshaft.

11. The catheter assembly of claim 10, further comprising a sheath disposed over the lumen, the sheath extending over at least a portion of the longitudinal length of the catheter.

12. The catheter assembly of claim 11, wherein a plate of the at least one rotating capacitor comprises the sheath.

13. The catheter assembly of claim 12, wherein the sheath is configured and arranged to couple to the system ground.

14. The catheter assembly of claim 1, wherein the at least one rotating capacitor comprises at least one dielectric material sandwiched between the at least one rotating plate and the at least one stationary plate.

15. An intravascular ultrasound imaging system comprising:
    a catheter having a longitudinal length, a distal end, and a proximal end, the catheter comprising
        a lumen extending along the longitudinal length of the catheter from the proximal end to the distal end, and
        a sheath disposed over the lumen, the sheath extending over at least a portion of the longitudinal length of the catheter;
    an imaging core configured and arranged for inserting into the lumen, the imaging core comprising
        a rotatable driveshaft having a distal end and a longitudinal length,
        at least one transducer mounted to the distal end of the rotatable driveshaft, the at least one transducer configured and arranged for transforming applied electrical pulses to acoustic pulses and also for transforming received echo pulses to electrical pulses,
        at least two conductors coupled to the at least one transducer and forming an electrical path to and from the at least one transducer, the at least two conductors extending along the longitudinal length of the driveshaft, and a conductive shield disposed around a portion of each of the at least two conductors a shield-coupling capacitor electrically coupled to the conductive shield and to a system ground, the shield-coupling capacitor comprising at least one rotating capacitor, the at least one rotating capacitor comprising at least one rotating plate and at least one stationary plate; and a control module coupled to the imaging core, the control module comprising a pulse generator configured and arranged for providing electric pulses to the at least one transducer, the pulse generator electrically coupled to the at least one transducer via the one or more conductors, and a processor configured and arranged for processing received electrical pulses from the at least one transducer to form at least one image, the processor electrically coupled to the at least one transducer via the one or more conductors.

16. The intravascular ultrasound imaging system of claim 15, wherein the control module further comprises at least one display electrically coupled to the processor, the at least one display configured and arranged for displaying the at least one image formed by the processor.

17. The intravascular ultrasound imaging system of claim 15, wherein the shield-coupling capacitor further comprises a high-voltage capacitor in series with the rotating capacitor.

18. A method for imaging a patient using an intravascular ultrasound imaging system, the method comprising:

inserting a catheter into patient vasculature, the catheter comprising an imaging core electrically coupled to a control module by at least two conductors disposed partially within a conductive shield, the at least two conductors forming an electrical path to and from the imaging core;

positioning the imaging core in a region to be imaged;

transmitting at least one electrical pulse from the control module to the imaging core over the at least two conductors;

receiving at least one echo signal from a tissue-boundary between adjacent imaged patient tissue by the imaging core;

transmitting at least one transformed echo signal from the imaging core, over the at least two conductors, to the control module for processing; and shunting electrical noise coupling to the transformed echo signal to a system ground via a shield-coupling capacitor electrically coupled to the conductive shield, the shield-coupling capacitor comprising at least one rotating capacitor.

19. The method of claim 18, wherein the shield-coupling capacitor further comprises a high-voltage capacitor in series with the rotating capacitor, the capacitance of the high-voltage capacitor adjusted to limit patient exposure to potential current leakage between the shield-coupling capacitor and the system ground when the high-voltage capacitor is positioned in series with the rotating capacitor.

* * * * *